US012188002B2

(12) United States Patent
Yeo et al.

(10) Patent No.: US 12,188,002 B2
(45) Date of Patent: Jan. 7, 2025

(54) SENSING SYSTEMS

(71) Applicant: Georgia Tech Research Corporation, Atlanta, GA (US)

(72) Inventors: Woon-Hong Yeo, Atlanta, GA (US); Yun-Soung Kim, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 645 days.

(21) Appl. No.: 16/786,398

(22) Filed: Feb. 10, 2020

(65) Prior Publication Data

US 2020/0255791 A1 Aug. 13, 2020

Related U.S. Application Data

(60) Provisional application No. 62/802,985, filed on Feb. 8, 2019.

(51) Int. Cl.
*C12M 1/34* (2006.01)
*A61B 5/145* (2006.01)
*C12M 1/00* (2006.01)

(52) U.S. Cl.
CPC ......... *C12M 41/26* (2013.01); *A61B 5/14532* (2013.01); *C12M 23/14* (2013.01)

(58) Field of Classification Search
CPC ...... C12M 41/26; C12M 23/14; C12M 27/16; A61B 5/14532; A61B 5/0002; A61B 5/01; A61B 5/14539; A61B 5/1486; A61B 2562/066

See application file for complete search history.

(56) References Cited

U.S. PATENT DOCUMENTS

| 5,791,344 A * | 8/1998 | Schulman ........... A61B 5/14865 600/347 |
| 8,852,921 B2 * | 10/2014 | Rao ........................ C12M 23/00 435/288.1 |
| 9,423,351 B2 * | 8/2016 | Barnfield Frej ....... C12M 41/00 |
| 11,008,542 B2 * | 5/2021 | Kaisermayer .......... C12M 41/00 |
| 2002/0137991 A1 * | 9/2002 | Scarantino ......... A61B 5/14865 600/300 |
| 2005/0163667 A1 * | 7/2005 | Krause .................... B01L 3/505 422/400 |
| 2005/0272146 A1 * | 12/2005 | Hodge .................. B01F 35/513 435/289.1 |
| 2015/0141767 A1 * | 5/2015 | Rogers ................. A61B 5/6885 600/361 |
| 2016/0066789 A1 * | 3/2016 | Rogers ................... A61B 5/685 604/20 |
| 2017/0122783 A1 * | 5/2017 | Xue ......................... G01K 7/22 |
| 2018/0263539 A1 * | 9/2018 | Javey ................... A61B 5/1477 |

\* cited by examiner

*Primary Examiner* — William H. Beisner
*Assistant Examiner* — Danielle B Henkel
(74) *Attorney, Agent, or Firm* — Troutman Pepper Hamilton Sanders LLP; Ryan A. Schneider; Brandon M. Reed

(57) ABSTRACT

A thin, soft sensor array system that can be deployed over the surfaces of bag bioreactors. The sensor array is fabricated using microfabrication processes along with functionalization methods necessary for measuring pH, glucose, and temperature. Miniature integrated circuit (IC) components are incorporated with the thin-film circuits, allowing for the real-time, on-board data analysis and wireless data communication.

13 Claims, 18 Drawing Sheets

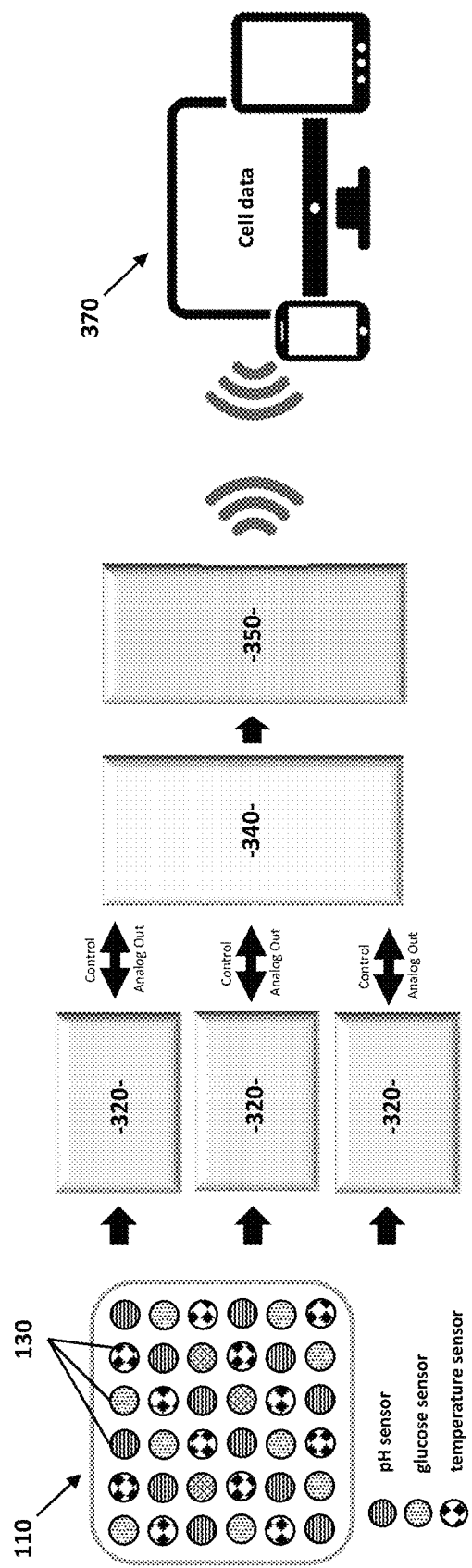

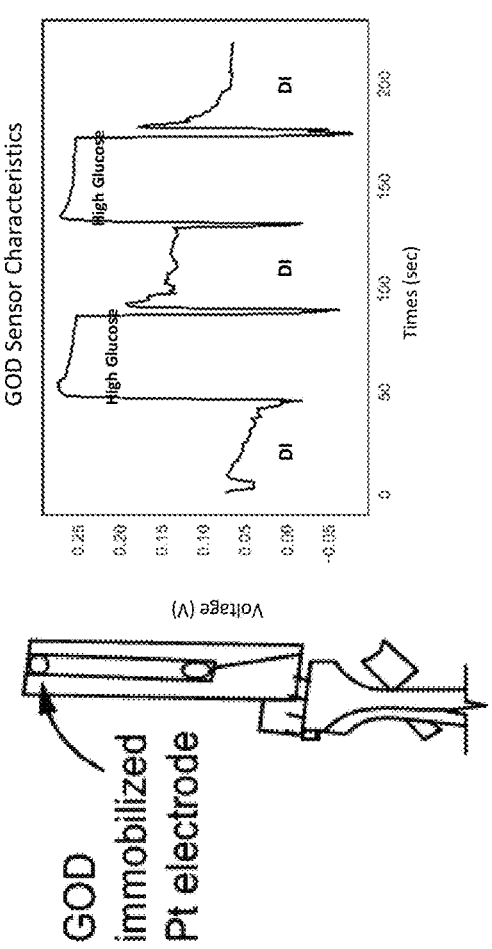
FIG. 5D
FIG. 5C
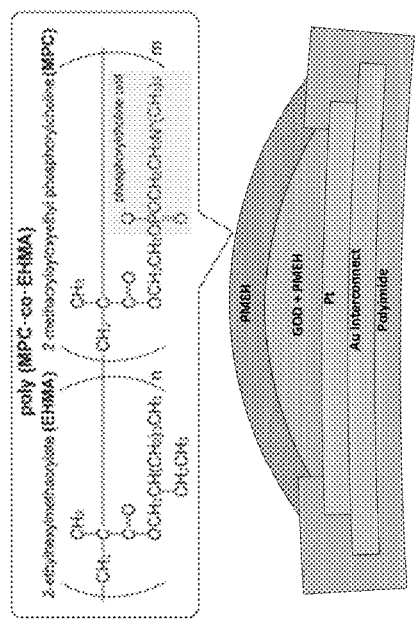
FIG. 5A
FIG. 5B

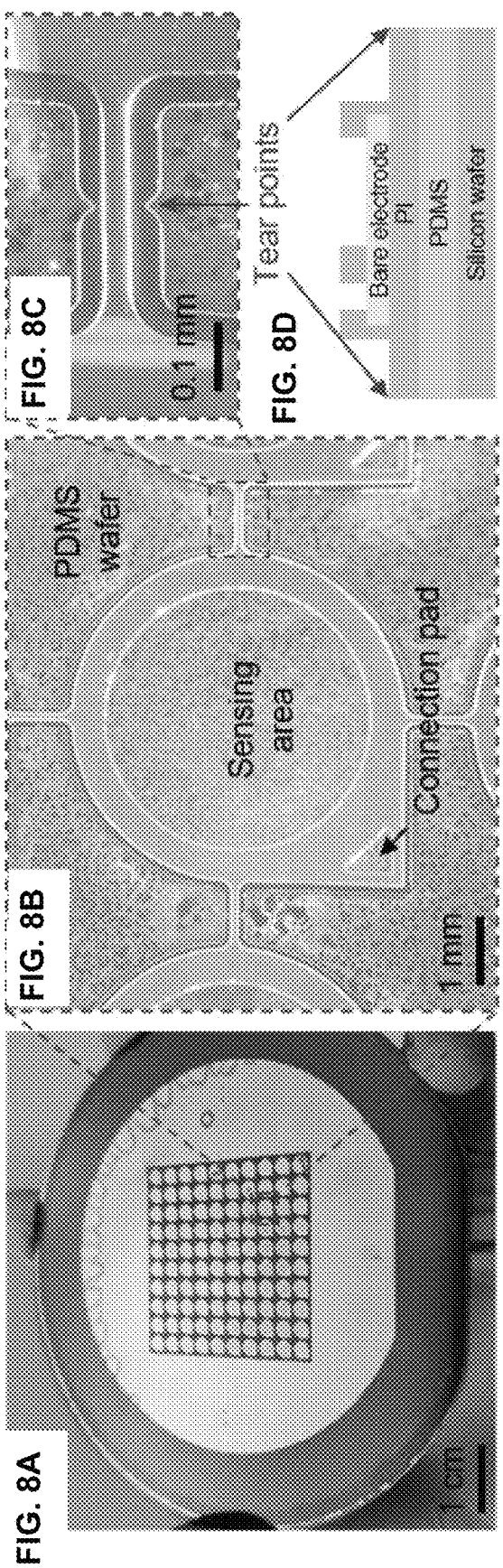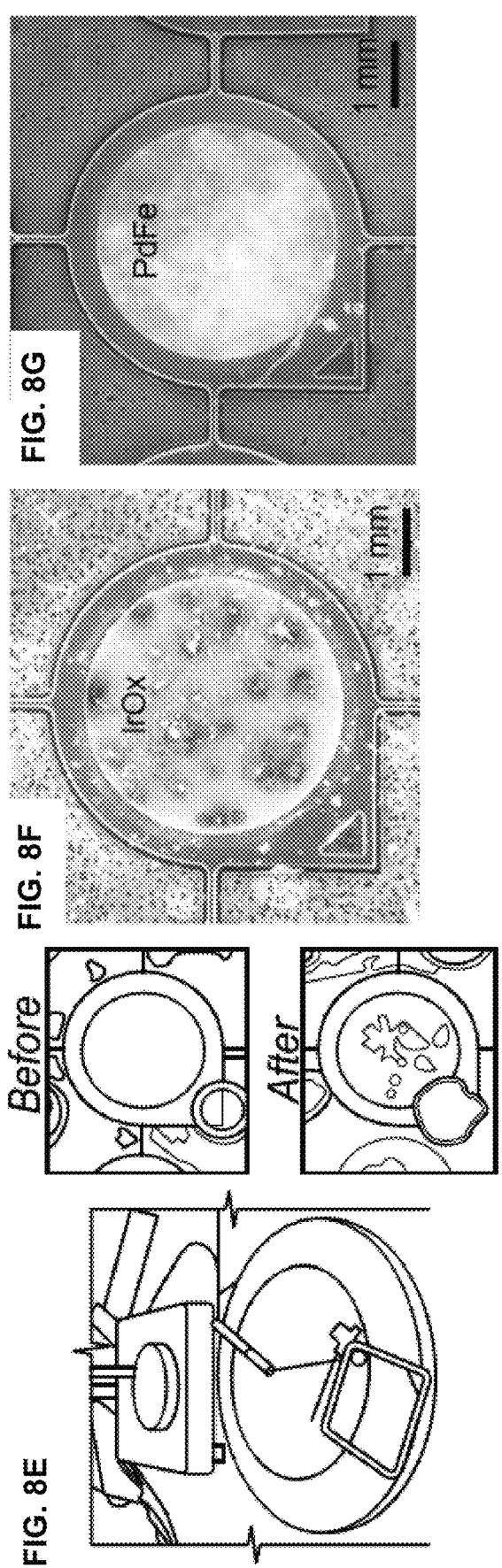

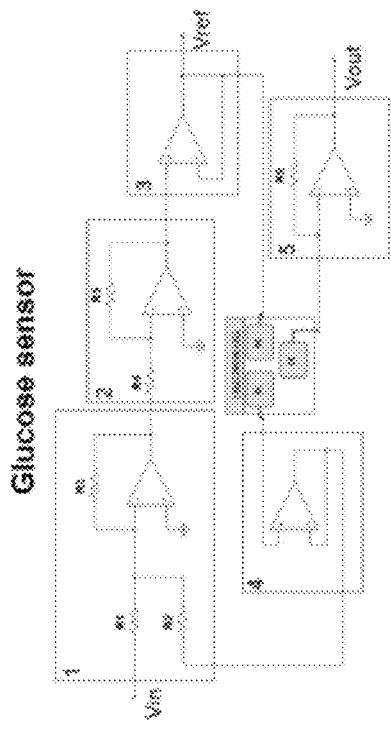
Fig. 10A Temp sensor
Fig. 10B pH sensor
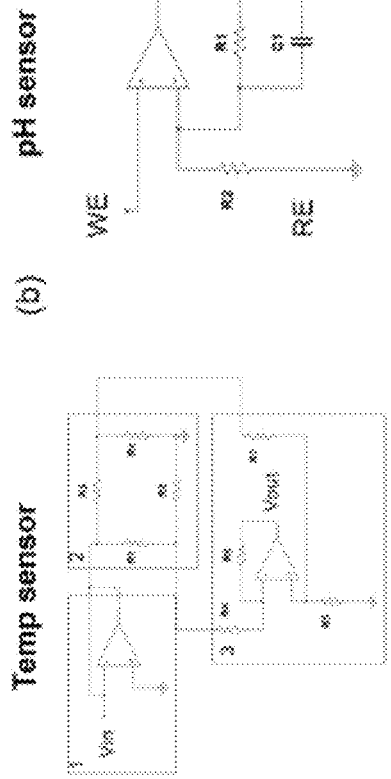
Fig. 10C Glucose sensor
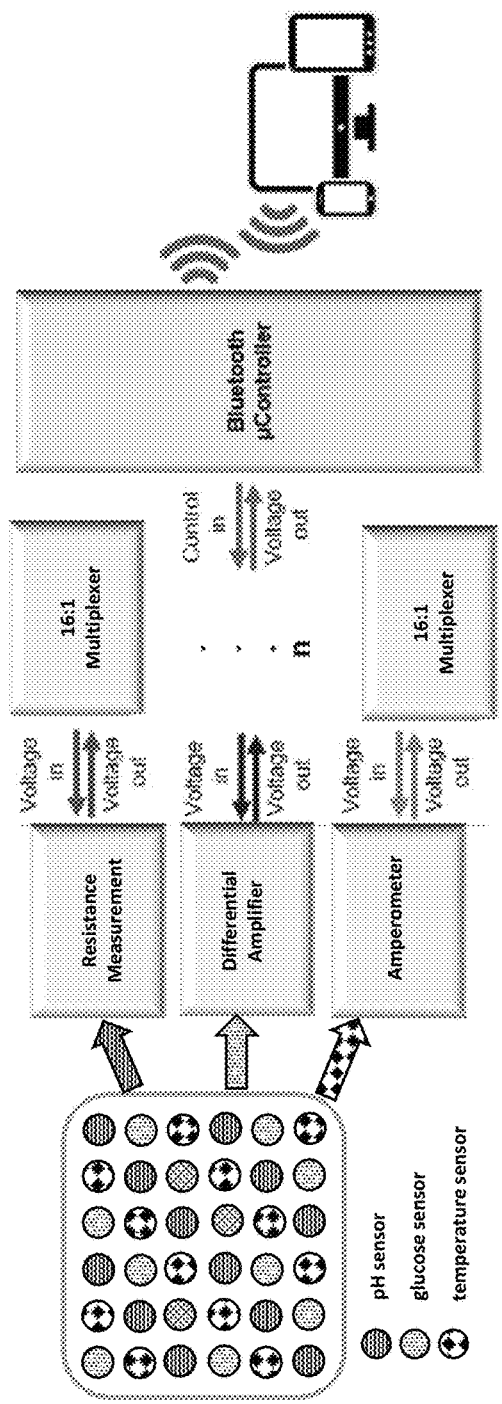
Fig. 10D

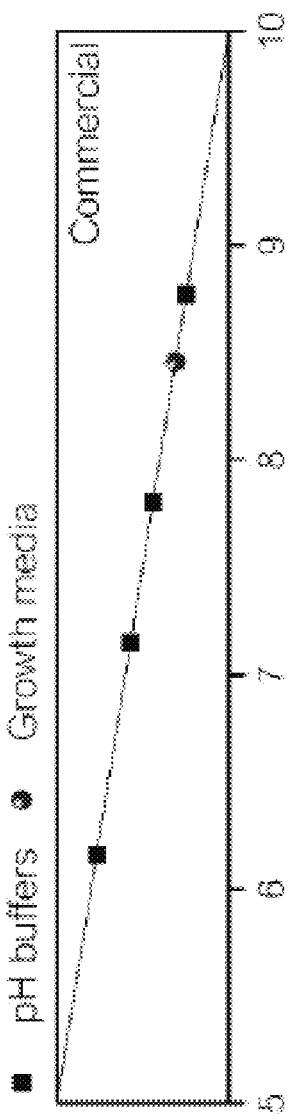
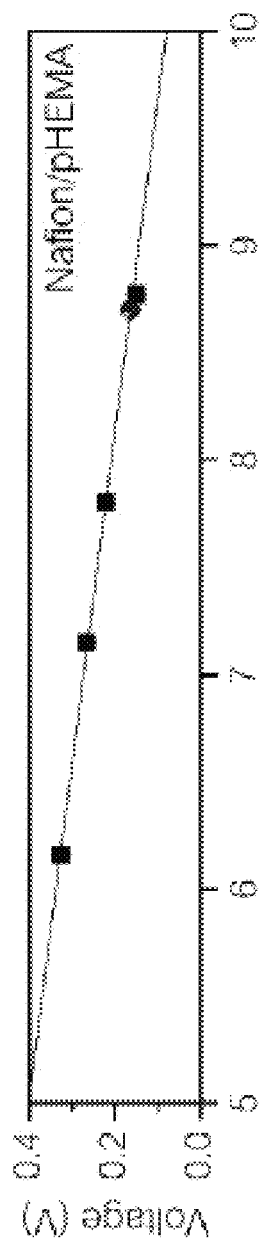
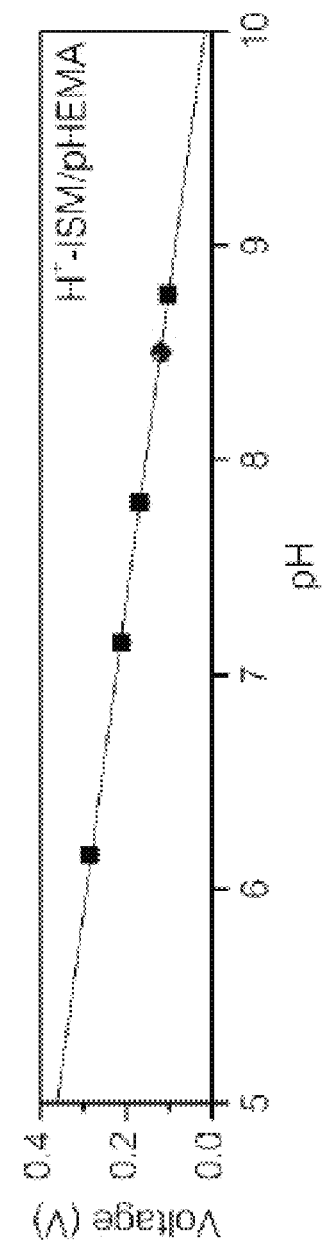
FIG. 13A
FIG. 13B
FIG. 13C

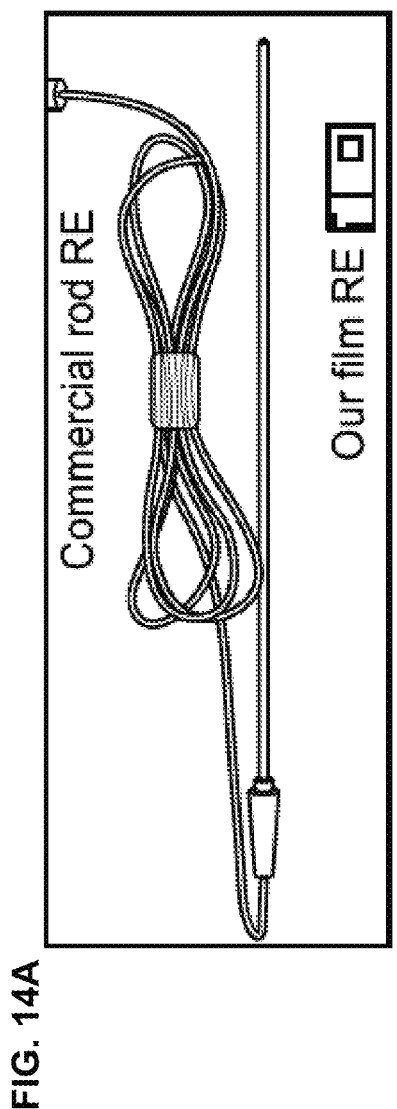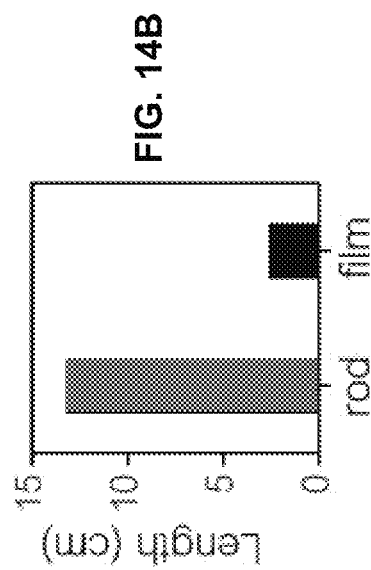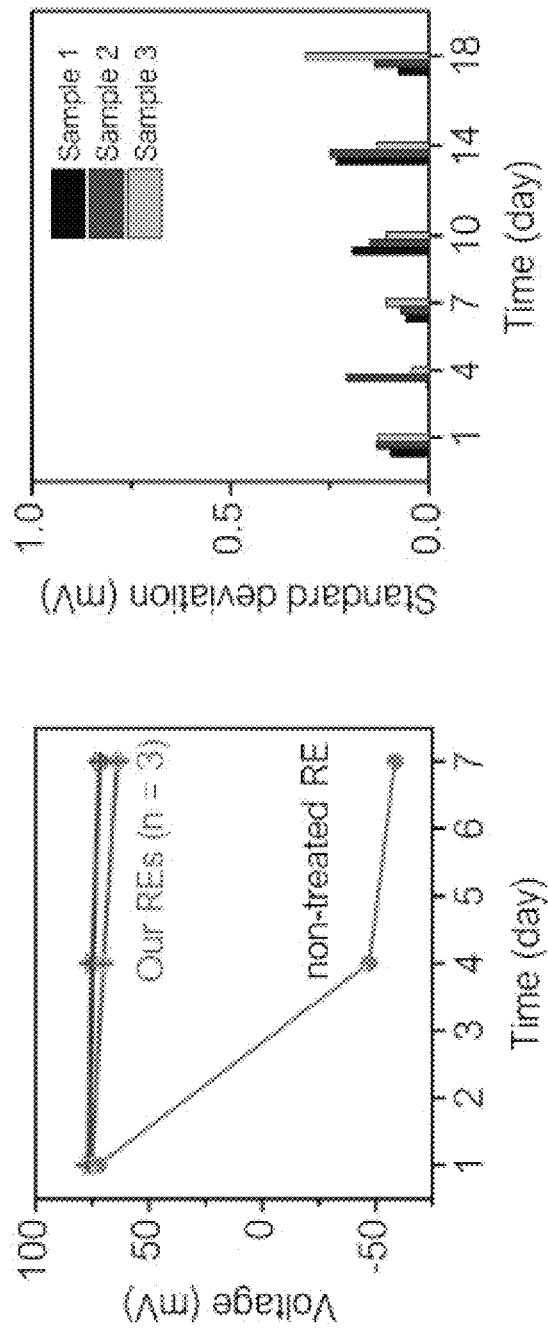
FIG. 14A
FIG. 14B
FIG. 14C
FIG. 14D

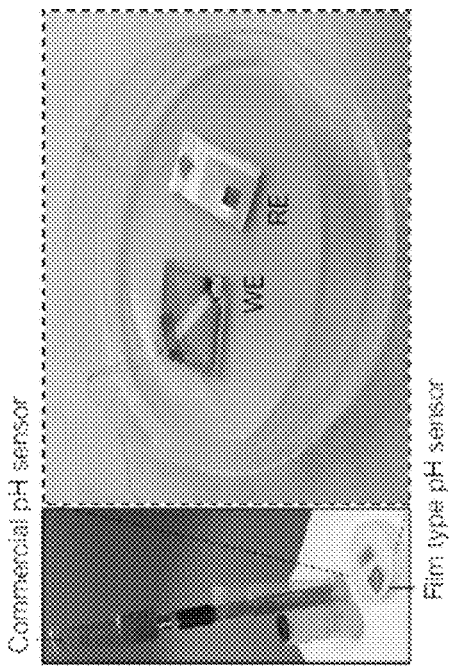
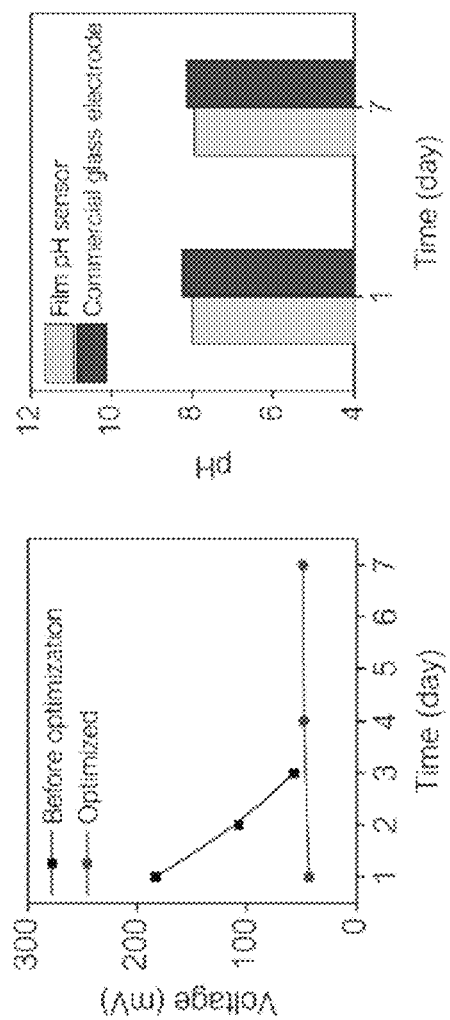
FIG. 16A
FIG. 16B
FIG. 16C

SENSING SYSTEMS

CROSS-REFERENCE TO RELATED APPLICATIONS

This application claims the benefit of U.S. Provisional Patent Application No. 62/802,985, filed 8 Feb. 2019, the entire contents and substance of which are hereby incorporated by reference as if fully set forth below.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A JOINT INVENTOR

Not Applicable

BACKGROUND OF THE INVENTION

Single-use bioreactors are widely used in the field of mammalian cell culture. Instead of a culture vessel made from stainless steel or glass, a single-use bioreactor is equipped with a disposable bag. The disposable bag is usually made of a three-layer plastic foil. One layer is made from polyethylene terephthalate (PET) or low-density polyethylene (LDPE) to provide mechanical stability. A second layer made using polyvinyl acetate (PVA) or polyvinyl chloride (PVC) acts as a gas barrier. A third contact layer is made from PVA or polypropylene (PP).

There are generally two different approaches for constructing single-use bioreactors, differing in the means used to agitate the culture medium. Some single-use bioreactors use stirrers that are integrated into the plastic bag. The closed bag and the stirrer are pre-sterilized. In use the bag is mounted in the bioreactor and the stirrer is connected to a driver mechanically or magnetically.

Another single-use bioreactor is agitated by a rocking motion. This type of bioreactor does not need any mechanical agitators inside the single-use bag. The flexible disposable bioreactor for culturing cells in a liquid medium use of an inflated plastic bag that provides a sterile, disposable cultivation chamber for various types of cells. The bag is placed on a rocking platform to induce a gentle wave-like motion to the liquid contained therein, providing liquid mixing and enhancing oxygen transfer from the headspace gas to the liquid phase where it is essential for cell growth and metabolism.

Bioreactors can be used with many types of biologically active environments. For example, bag-type film bioreactors have been adopted by commercial stem cell (SC) manufacturing due to the large maximum volume per system as well as the relatively effective isolation of the cell cultures.

Personalized medicine based on SCs increasingly holds promise for providing cures for many intractable neurodegenerative and genetic diseases. SCs, such as primary mesenchymal stem cells (MSCs) and muscle stem cells (MuSCs) have become the main therapeutic tools due to their pluripotency and regenerative capacity.

When derived from the patient, these SCs can be induced to necessary cell type and state, and administered back to the patient, creating a patient-specific therapy with a minimal immune response. Yet, there is not at this time widespread SC-based therapies as a standard of care for disease treatment. Besides the regulatory hurdles, the key bottleneck preventing the translation of SC therapies in clinical applications is the lack of a manufacturing platform that guarantees the production of clinical-grade SCs with high reproducibility and cell state maintenance. While the scale-up of cell production can meet the demand of the number of cells, maintaining the qualities of the cells over large areas, throughout the processing period, pose as the engineering challenge.

However, conventional monitoring of the cell cultures in bag-type bioreactors rely on individual optical "spot" sensors providing culture information only near the sensor. Moreover, the optical sensing requires additional modules and dedicated data acquisition systems, which can be cost-prohibitive and technically challenging to incorporate multiple sensors.

It would be beneficial to provide an engineering solution to the challenges associated with the monitoring of large area cell cultures. It is an objective of the present invention to provide such a solution.

BRIEF SUMMARY OF THE INVENTION

Cell bag bioreactors agitated by a rocking motion have been the well-known cell manufacturing method since they allow for large-scale cultivation at lowered maintenance and cost. Due to the increased demand for various cell types manufacturers of the bioreactors are now offering bioreactors with volume capacity up to 200 L. In order to ensure the uniform distribution of the cell medium, the bioreactors are continuously agitated by a rocking motion, or by a stirrer. The conventional method for monitoring the culture conditions relies on a single sensor unit per modality, characterizing the culture's properties only around the sensor.

In an exemplary embodiment, the present invention is a sensing system comprising a telemetry unit and a multimodal sensing platform, wherein the sensing system is configured to provide wireless real-time data representative of modalities of a biologically active environment to which the sensing system is in monitoring contact.

The modalities of the biologically active environment can be selected from the group consisting of pH, glucose level, and temperature of the biologically active environment.

The telemetry unit can be encapsulated within a silicon-based elastomer. The multimodal sensing platform can be encapsulated within a biocompatible polymer.

The multimodal sensing platform can comprise an open-mesh serpentine network.

The multimodal sensing platform can comprise pH sensors comprising an iridium oxide ($IrO_x$) film deposited on a platinum electrode. The multimodal sensing platform can comprise glucose sensors comprising glucose oxidase enzyme (GOD) and a platinum electrode. The multimodal sensing platform cam comprise temperature sensors comprising a thin-film platinum electrode.

In another exemplary embodiment, the present invention is a bioreactor system comprising a flexible bioreactor configured to contain a biologically active environment and the sensing system disclosed above, wherein at least a portion of the multimodal sensing platform is configured to be in monitoring contact with the biologically active environment.

In another exemplary embodiment, the present invention is a bioreactor system for the cultivation of stem cells comprising a flexible bioreactor configured for the cultivation of stem cells and the sensing system disclosed above, wherein the biologically active environment is configured for the cultivation of stem cells, and wherein at least a portion of the multimodal sensing platform is configured to be in monitoring contact with the biologically active environment.

In another exemplary embodiment, the present invention is a thin, soft sensor array system, which can be deployed over the surfaces of the bag bioreactors. The sensor array is fabricated using microfabrication processes along with functionalization methods necessary for measuring pH, glucose, and temperature. Miniature integrated circuit (IC) components are directly incorporated with the thin-film circuits, allowing for the real-time, on-board data analysis and wireless data communication.

Serpentine design layout and encapsulation strategies with silicone-based elastomer allows the sensor system to achieve specific elasticity and modulus, which are critical mechanical characteristics for platforms interfacing stem cell cultures. The thin and soft sensor system provides the means to monitor large area culture qualities through the spatial sensing capabilities, culture compatibility, and scalability.

The present invention is a soft hybrid electronic system equipped with an array of three sensor types (glucose, pH, temperature) that span the internal surface of the bag's lower membrane. The multi-sensor arrangement provides the platform capable of continuous, time-dynamic, and spatial variation of the culture conditions that was not possible with conventional systems. Due to the thin, open-mesh serpentine network, the sensors system can be seamlessly incorporated into the bag's membrane, providing the minimum mechanical disturbance.

The present invention incorporates nanostructured membrane circuits, solid-state chemical sensors, elastomer, and electronic components to form a low-profile, flexible sensing system, which can be directly embedded into the bioreactor's membrane. The multi-sensor configured in an array format allows for the simultaneous monitoring of the cell culture's conditions over the surfaces covered by the sensor array. The onboard electronic components include a wireless communication (Bluetooth Low Energy (BLE)), an analog-to-digital converter (ADC), multiplexers, a microcontroller, and power management.

With these functions, the sensor system can transmit the real-time data wirelessly throughout the periods of cell manufacturing. The thin, open-mesh structure allows the sensing area to be seamlessly integrated with the cell bag, thereby maintaining the bioreactor's mechanical characteristics unperturbed. The thin circuitry is fully embedded in a biocompatible polymer (polyimide), and the chip components are encapsulated with silicon-based elastomer. This packaging strategy ensures that the addition of the sensor system does not result in negative outcomes in cell manufacturing. The cell bags equipped with the present invention is a "smart bioreactor" and provide the culture's real-time conditions with detail spatial information.

The thin-film flexible electronic circuit is formed using microfabrication processes, allowing the circuit's thickness to be only 5 µm in an exemplary embodiment. The sensor system is integrated in the cell bag's lower membrane and interacts directly with the cell culture. The smart bioreactor is compatible with commercially available rocking unit, hence there is no additional cost involved with re-engineering the accessory equipment.

In another exemplary embodiment, the sensor arrangement and the data processing scheme includes a 6×6 sensor array of three kinds of sensors distributed over 10 cm×10 cm area. Multiplexers serially address the 36 channels and pass the analog data to the ADC. The BLE programmable-system-on-chip then wirelessly transmits the data to the connected smart device. The use of multiplexers significantly reduces the number of wires needed to address all 36 sensors. The multiplexing speed can be tuned based on the user's requirement.

The fabrication methods and characteristics of three exemplary sensor types includes layers of polyimide and sputter-deposited conductors/electrodes being structured using microfabrication processes, such as spin-coating, sputter deposition, reactive ion etching, and wet etching. For pH and glucose sensor types, the platinum electrode is functionalized with iridium oxide and glucose oxidase, respectively. For temperature sensing, a Texas Instruments' LMT70 chip is soldered directly onto the flexible circuit platform.

BRIEF DESCRIPTION OF THE SEVERAL VIEWS OF THE DRAWING

FIGS. 3A-3E illustrate sensor data process flow in accordance with one or more exemplary embodiments of the present invention.

FIGS. 5A-5D illustrate the fabrication and characterization of an inventive glucose sensor in accordance with one or more exemplary embodiments of the present invention.

FIGS. 8A-8G illustrate wafer-level fabrication of the solid-state sensor arrays in accordance with one or more exemplary embodiments of the present invention.

FIGS. 10A-10C are circuit designs of the thin-film solid-state sensors of FIGS. 4A-4D, FIGS. 5A-5D, and FIGS. 6A-6D, and FIG. 10D is an overall block diagram of the present smart bioreactor sensor circuity in accordance with one or more exemplary embodiments of the present invention.

FIG. 12A shows a linear sweep voltammogram of an Au electrode in an $IrO_x$ depositing solution. FIG. 12B illustrates the effect of applying voltages of pulsed electrodeposition for stability of $IrO_x$ film sensor (unstable surface: $V_{ON}$=0.8 V, stabilized: $V_{ON}$=0.9 V). FIG. 12C shows a linear voltage response in a subtle pH range. FIG. 12D is the measured voltage and calculated pH values of the stabilized film sensor. Each is in accordance with one or more exemplary embodiments of the present invention.

FIGS. 13A-13C illustrate the improved accuracy of the pH electrode by adopting ion-selective membrane, in accordance with one or more exemplary embodiments of the present invention.

FIGS. 14A-14D show the improved stability of film type reference electrode (RE).

FIGS. 14A-14B show the smaller form factor of the present film RE that is adaptable for a bioreactor. FIG. 14C illustrates the long-term stability of the voltage signal of the present REs after annealing and chemical stabilizing steps. The voltage was measured in PBS solution. FIG. 14D illustrates the stable film RE showing a small voltage deviation (<0.5 mV) for 18 days. Each is in accordance with one or more exemplary embodiments of the present invention.

FIG. 15A are cell culture plates with different membranes coated on the bottom. FIG. 15B illustrates the multi-well cell culture plates coated with different membranes. FIG. 15C illustrates the different membranes coated on $IrO_x$ film sensor positioned on the bottom of the culture plates. Each is in accordance with one or more exemplary embodiments of the present invention.

FIGS. 16A-16C show the stability of the present pH sensor in C2C12 cell media. FIG. 16A shows voltage signals measured with an unstable $IrO_x$ electrode and an inventive pH sensor with stabilized and biocompatible surfaces. FIG. 16B illustrates calculated pH values from the voltages measured with the present film electrode compared to a glass electrode. FIG. 16C is a photo of the pH electrode and film type pH sensor immersed in pH 7 buffer as an example measurement. Film electrodes are fixed on the bottom of cell culture dish. Each is in accordance with one or more exemplary embodiments of the present invention.

FIG. 17A is a photo of a pH electrode fixed on a 24-well cell plate with 5 k MuSC. FIG. 17B shows cell viability of the pH electrode compared to control media. FIG. 17C shows voltage measured for 30 minutes in the MuSC media with the film pH senor. Each is in accordance with one or more exemplary embodiments of the present invention.

FIG. 18A includes micrographs of the morphology of a PdFe film sensor with and without coating a membrane on the top. FIG. 18B shows chronoamperometry measured at an applied voltage of −0.01 V. FIG. 18C illustrates different voltage response to 1-55 mM glucose under −0.01 to −0.5 V conditions.

DETAILED DESCRIPTION OF THE INVENTION

Figure 1:
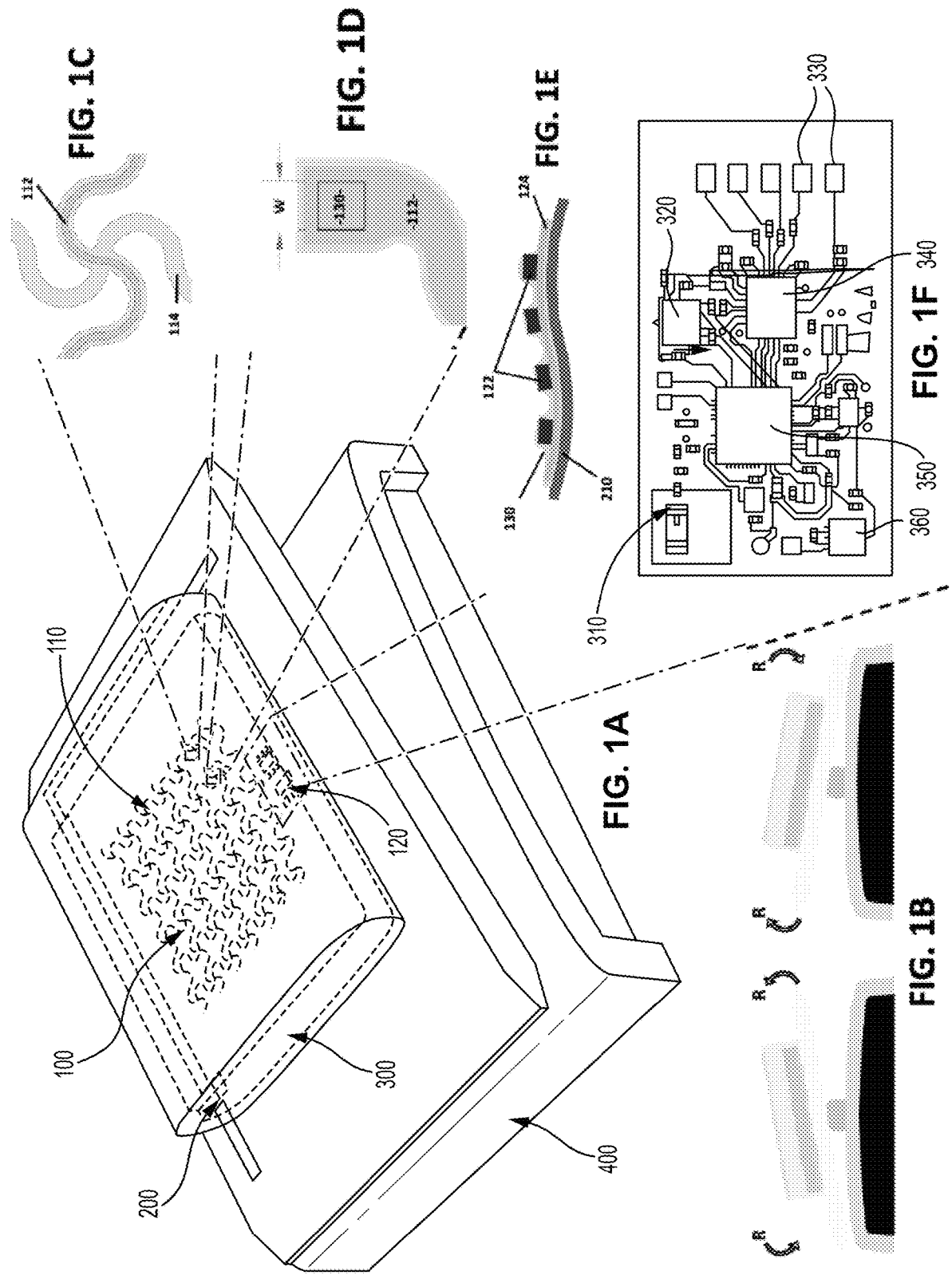
FIGS. 1A-1F illustrate a system overview including illustrations of a bioreactor and rocking unit (FIGS. 1A-1B), a magnified view of the interconnects and sensors of the multimodal sensing platform (FIGS. 1C-1D), and a side and top view of the telemetry unit (FIGS. 1E-1F), all in accordance with one or more exemplary embodiments of the present invention.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

As shown in FIGS. 1A-1F, the present invention is an engineering solution to the challenges associated with monitoring of large area cell cultures with the innovative use of a sensing system 100 comprising a multimodal sensing platform 110 comprising an open-mesh structure and a telemetry unit 120. The multimodal sensing platform can be a thin, soft sensor array system that can be deployed over the surfaces 210 of bag bioreactors 200. The sensor array can be fabricated using microfabrication processes along with functionalization methods necessary for measuring different modalities of the cell culture 300 in the bag bioreactor 200, for example, the pH, glucose, and temperature. A serpentine design layout 112, 114 and encapsulation strategy 130 with silicone-based elastomer can allow the sensor system to achieve specific elasticity and modulus, which are preferential mechanical characteristics for the present thin and soft sensor system to enable it to provide the means to monitoring large area culture qualities through the spatial sensing capabilities, culture compatibility, and scalability.

The telemetry unit 120 can include miniature integrated circuit (IC) components 122 directly incorporated with thin-film circuits 124, allowing for the real-time, on-board data analysis and wireless data communication. The telemetry unit 120 can comprise an antenna circuit 310, multiplexer 320, connections 330 to the sensing platform 110, an amplifier 340, a Bluetooth chip 350 and a voltage regulator 360.

The telemetry unit 120 was based on a circuit design developed for a rigid prototype board, and a fabrication and assembly process was invented to complete a flexible wireless telemetry unit. As shown in FIG. 1F, the telemetry unit comprises surface mount chip components necessary for Bluetooth Low Energy, a 2.4 GHz antenna circuit, voltage regulation, multiplexing, and analog-to-digital conversion. Structurally, the unit 120 comprises a thin-membrane, multilayer copper/polyimide composite interconnection platform, miniature chip components, and elastomeric encapsulation. The interconnection platform was fabricated and completed thin-film was transferred from the PDMS-coated substrate and transferred to a glass slide, where the surface mount chip components are integrated using reflow soldering technique. Finally, the soldered thin-film structure is encapsulated with a low modulus elastomer (Ecoflex 0300, Smooth-On) for full isolation of the electronics. The fully assembled telemetry unit has flexibility and compliant mechanical properties to bend naturally with the underlying surface.

FIGS. 1A-1F show an overview of the present system 100 and its application in a bioreactor 200. The thin-film flexible electronic circuit 124 is formed using microfabrication processes, allowing the circuit's thickness to be only 5 µm. The sensor system is integrated in the cell bag's lower membrane and interacts directly with the cell culture. The smart bioreactor is compatible with an available rocking unit 400, hence there is no additional cost involved with re-engineering the accessory equipment.

Figure 2:
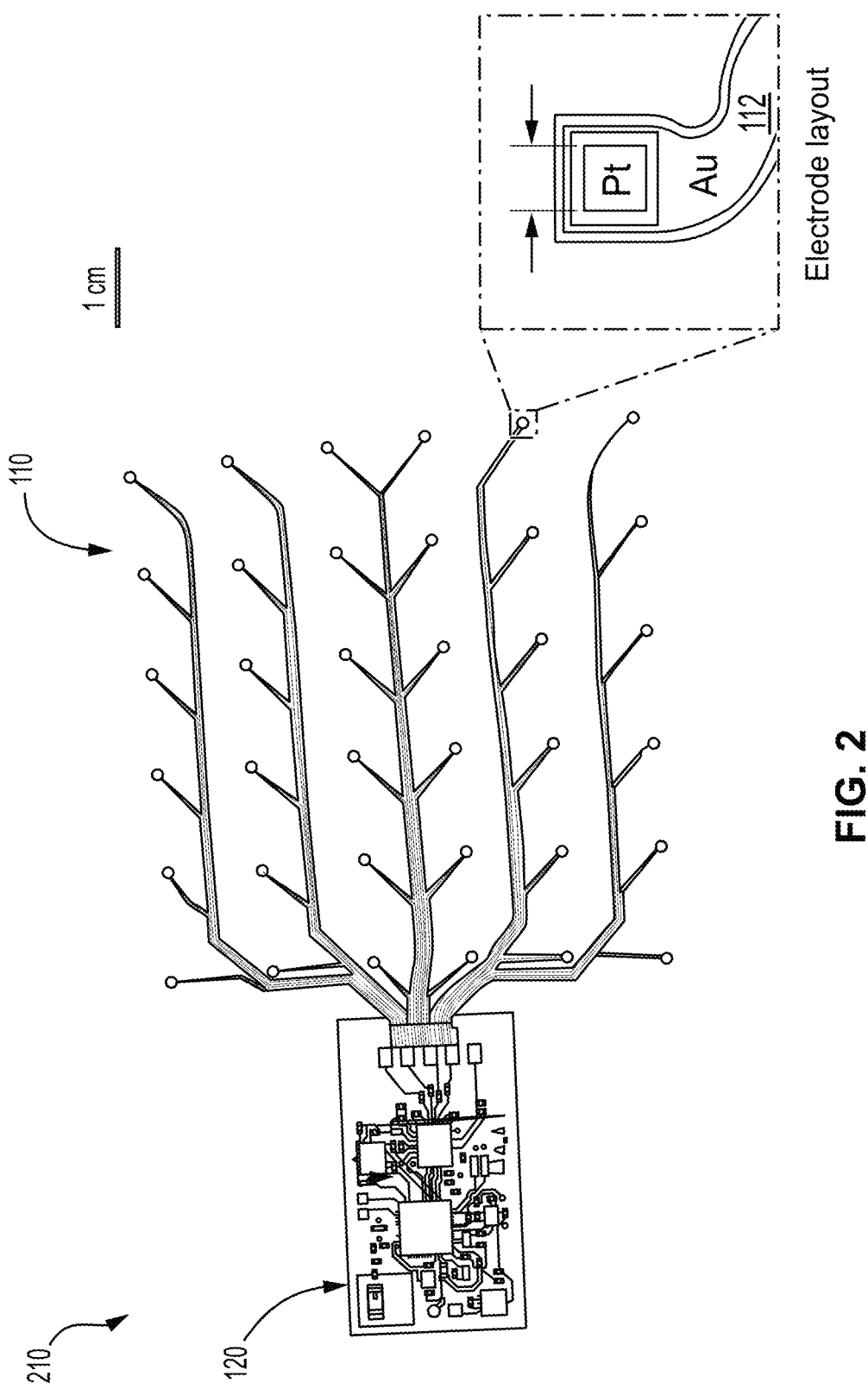
FIG. 2 is a photo of a sensor array and its integration with the bioreactor membrane in accordance with one or more exemplary embodiments of the present invention.

FIG. 2 illustrates a fully assembled sensing system 100 integrated onto the inner surface 210 of a bag bioreactor.

For the fabrication of the multimodal sensing platform 110, aerosol jet printing was used (Optomec Aerosol Jet 200, Optomec), a type of additive manufacturing method superior to inkjet printing owing to its ability to print a wide range of materials choice and ink concentration. A poly(methyl methacrylate)-coated four-inch silicon wafer was used as the sacrificial surface to print the sensor array structure using polyimide (PI-2545, HD Microsystems) ink diluted with N-Methyl-2-pyrrolidone (NMP). Upon curing the printed polyimide pattern in a 250° C. oven for two hours, Ag nanoparticle (Ag40XL, UT Dots) mixed with xylene (m-Xylene, Sigma-Aldrich) was printed and sintered at 240° C. for one hour to form the conductive traces.

The top PI is subsequently printed and cured for electrical isolation. Once the additive steps are completed, the sensor structure is transferred to a thin sheet of elastomer substrate. Finally, the necessary electrochemistry and surface functionalization steps for two exemplary chemical sensor types (glucose, pH) take place to complete the sensor functionalization. FIG. 2 is a photo of the sensor array and its integration with the bioreactor membrane 210.

FIGS. 3A-3E schematically illustrate the sensor arrangement (FIG. 3A) and the data processing scheme (FIGS. 3B-3E). An exemplary 6×6 sensor array 110 has three representative kinds of sensors 130 distributed over 10 cm×10 cm area. Three multiplexers 320 (for example, two 16:1 and one 4:1) serially address the 36 channels and pass the analog data to an analog-to-digital converter (ADC) 340. The Bluetooth enabled programmable-system-on-chip 350 then wirelessly transmits the data to a connected smart device 370. The use of multiplexers 320 significantly reduces the number of wires needed to address all 36 sensors 130. The multiplexing speed can be tuned based on the user's requirement.

Figures 4A, 4B, 4C, 4D:
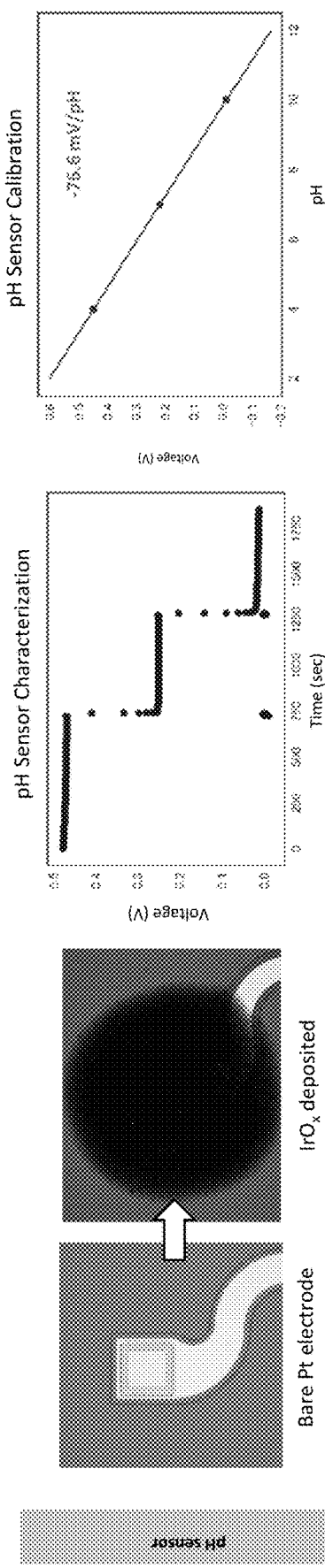
FIGS. 4A-4D illustrate the fabrication and characterization of an inventive pH sensor in accordance with one or more exemplary embodiments of the present invention.
Figures 6A, 6B, 6C, 6D:
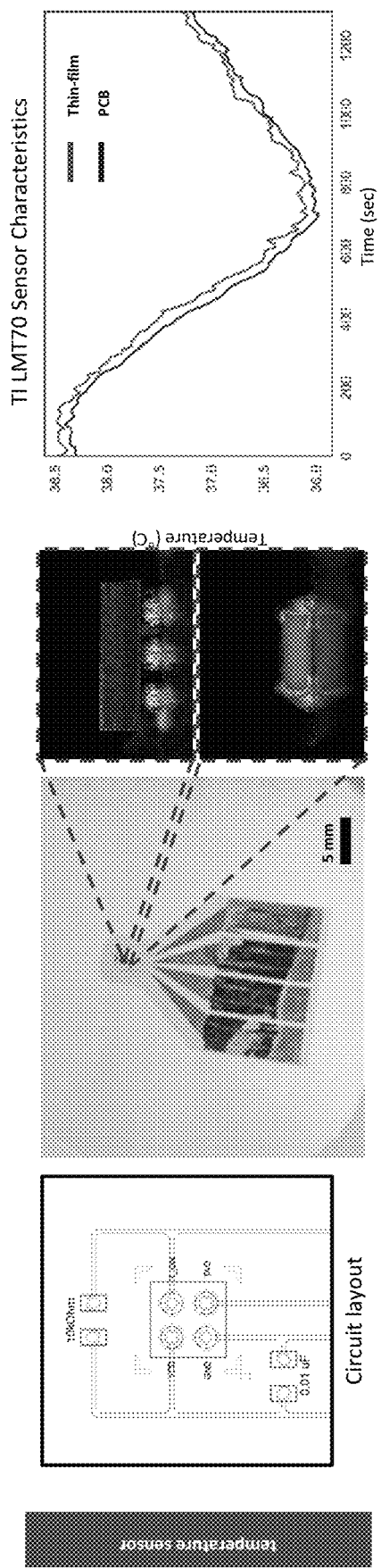
FIGS. 6A-6D illustrate the fabrication and characterization of an inventive temperature sensor in accordance with one or more exemplary embodiments of the present invention.

FIGS. 4-6 illustrate fabrication methods and the characteristics of three sensor types (FIGS. 4A-4D—pH sensor; FIGS. 5A-5D—glucose sensor; and FIGS. 6A-6D—temperature sensor). For all three sensors, layers of polyimide and sputter-deposited conductors/electrodes were structured using microfabrication processes, such as spin-coating, sputter deposition, reactive ion etching, and wet etching. For pH and glucose sensors, the platinum electrode is functionalized with iridium oxide and glucose oxidase, respectively. For temperature sensing, Texas Instruments' LMT70 chip is soldered directly onto the flexible circuit platform. The characteristics of the three sensor types are shown in the right-most figures.

FIGS. 4A-4B are optical micrographs showing the Pt electrodes before and after $IrO_x$ deposition. FIGS. 4C-4D illustrate the resulting pH sensor exhibited a linear, super-Nernstian response with fast response time.

In an exemplary embodiment, for pH sensing, an electrochemically deposited an iridium oxide ($IrO_x$) film was used for its wide pH response range, fast response time, and high pH sensitivity. The $IrO_x$ deposition solution was dispensed over the Pt electrodes to form a puddle, and a platinized titanium mesh electrode was brought to contact the top surface of the solution. A galvanostatic mode was applied using a power supply with 0.01 A, 1.0 V for 40 minutes. The resulting light-blue $IrO_x$ film exhibited the expected linear, super-Nernstian response (−76.6 mV/pH) when submerged in three buffer solutions with pH levels of 4.01, 7, and 10.01, verifying $IrO_x$'s excellent pH sensitivity.

FIGS. 5A-5B illustrate the chemistry and a cross-section diagram of the glucose sensor structure. A Poly(MPC-co-EHMA) (PMEH) overcoat provides the $H_2O_2$-permeable protection and is designed to stabilize the sensor output. FIG. 5D shows sensor response in a buffer solution to increasing glucose concentration.

In an exemplary embodiment, for glucose sensing, glucose oxidase (GOD) enzyme was employed and its production of hydrogen peroxide ($H_2O_2$) in the presence of glucose and oxygen, where the amperometric response is proportional to $H_2O_{02}$ concentration. In order to immobilize GOD to Pt electrodes, PMEH was synthesized and polymerized with 2-methacryloyloxyethyl phosphorylcholine (MPC) and 2-ethylhexyl methacrylate (EHMA), and it was used as a hydrogen permeable protection membrane for GOD. The active sensing material was prepared by mixing 5 mg of GOD and 10 µl of PMEH (10 wt % in ethanol) then applying it over the Pt electrode, followed by curing at 4° C. for three hours. To prevent enzyme leakage, PMEH solution was drop-casted over the sensor and cured at 4° C. for three hours.

To verify the functionality of the sensor, the sensor was submerged in a phosphate buffer solution and added 0.01 g of glucose. A commercial glucose sensor (GluCell® Glucose Monitoring System) was used to monitor the actual glucose concentration throughout the test. The sensor exhibited a transient response to the added glucose. For instance, while the potential increase of −2 mV could be detected from the initial addition of glucose, no meaningful sensor response could be measured from the second addition and on. Consequently, it is suspected that, despite the presence of PMEH as the immobilization enhancer as well as the protection layer, enzyme loss has occurred. Currently, the PMEH curing process is being optimized and the effect of PMEH curing to sensor's stability being validated.

In an exemplary embodiment, for temperature sensing, an analog temperature sensor was used in a miniature surface mount chip package (LMT70, Texas Instruments). The temperature sensor, along with a capacitor and a resistor, was integrated with a thin, flexible interconnection platform using reflow soldering. The flexible temperature sensor was submerged in a water bath for functional verification and its temperature reading was compared to its evaluation module (LMT70, Texas Instruments). As shown in FIG. 6D, the thin-film sensor's reading correlated well with that of the rigid PCB counterpart with the slight offset of ~0.1° C. between the two data. Overall, the fabricated sensor exhibited the sufficient sensitivity to the temperature fluctuation created with a heated water bath, demonstrating its capability as a temperature sensor for the smart bioreactor.

FIG. 6A is a circuit layout in the flexible substrate. FIG. 6B is a photograph of a single flexible temperature sensor with a fan-out pads for wire connection. The zoom-in images of FIG. 6C show the result of reflow-soldering chip components. FIG. 6D illustrate a heated water bath test of the thin-film and the evaluation module show that both sensors responded to temperature variation with high correlation.

The innovative sensing system 100 having the multi-modal sensing platform 110 is capable of monitoring cell quality in a large culture area. The thin, soft electronic structure allows the seamless integration with a bioreactor's membrane while the sensor array captures real-time spatial information of the cells with three sensor types, for example, pH, glucose, and temperature. The present monitoring method provides manufacturers with a type of culture information that was previously not available in conventional system, such as the spatial distribution of cell population and culture areas with non-desirable growth rates or cell state. The use of the sensor system can establish the new standards of large-scale cell manufacturing with increased yield and reproducibility.

The present fully integrated wireless sensing system has been implemented. FIGS. 2, 3A depicts such a system comprising the wireless telemetry unit 120 and the exemplary 6×6 sensor array 110. The two-dimensional distribution of the three sensor types is schematically illustrated in FIG. 3A. This is only an exemplary embodiment, and those of skill in the art understand that alternative distribution patterns and sensor densities have other beneficial culture qualities.

Figure 7A:
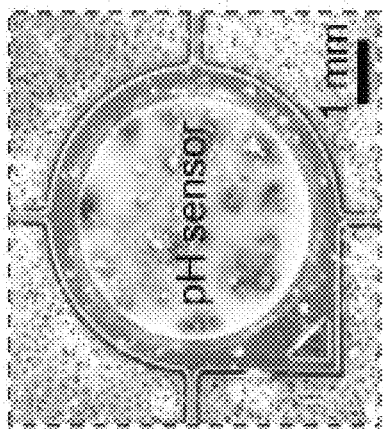
FIGS. 7A-7C are photos of the visual appearances of the three types of thin-film solid-state sensors of FIGS. 4A-4D, FIGS. 5A-5D, and FIGS. 6A-6D, in accordance with one or more exemplary embodiments of the present invention.
Figure 7B:
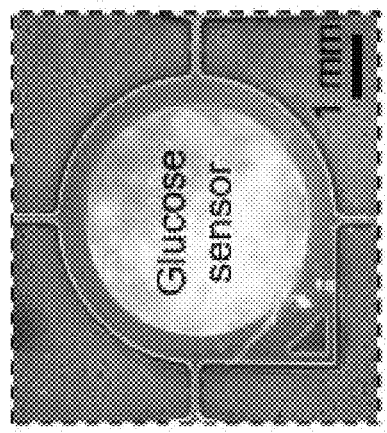
Figure 7C:
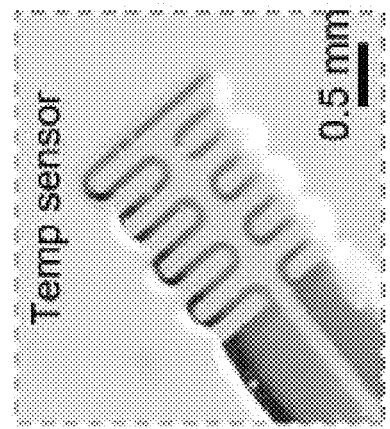

Optical microscope images shown in FIGS. 7A-7C illustrate the visual appearances of the three types of thin-film solid-state sensors used to monitor pH, glucose, and temperature. In an exemplary embodiment, all three types of sensors are manufactured using standard microfabrication processes along with additional electrochemical deposition steps for pH and glucose sensors for deposition of iridium oxide ($IrO_x$) and palladium iron (PdFe), respectively.

To demonstrate the capabilities of the sensing system toward continuous and wireless cell monitoring, a polystyrene Petri dish is integrated with the sensors followed by introduction of the medium containing muscle stem cells (MSC). Representative pH and glucose data collected during MSC growth exhibited good results.

Accurate, sensitive, and stable monitoring of various culture conditions require that the embedded sensors of the present invention exhibit consistent sensor-to-sensor characteristics when integrated over the bioreactor's membrane. Prior to the inventive techniques herein, manufacturing strategies were found lacking and not able to produce highly consistent thin-film, solid-state chemical sensors with intention to be transferred to flexible substrate.

The present invention further comprises novel microfabrication methods allowing wafer-scale manufacturing of solid-state pH and glucose sensors. It enables wafer-level electrodeposition of flexible solid-state chemical sensors for integration with the bag-embedded conductive traces.

As shown FIG. 8A, a four-inch polydimethylsiloxane (PDMS)-coated silicon wafer was used to pattern gold (or platinum) electrodes in the 10×10 array. The large region surrounding the electrode array is used to bond a wire. As shown in FIG. 8B, a closer inspection of an individual sensor design reveal that each 'pixel' contains the circular sensor area, exposed metal tab for the electrical connection with the bag-embedded interconnection, and four thin bridging traces to electrically connect adjacent pixels. To facilitate the tear-off of the selected sensor without affecting other sensors, the contour of the conductive bridges exhibits the shallowed polyimide (PI)'s width in the middle. The locations of such 'tear points' are also shown. (FIGS. 8C-D).

The electrochemical deposition of $IrO_x$ utilized a three-electrode configuration as shown in FIG. 8E, where the pulsed voltage (~700 mV squares every one second) is applied across the working electrode (WE), for example, exposed gold electrodes, and the counter electrode (CE), for example, a platinum (Pt)-coated wafer. For PdFe deposition, a negative voltage (~1 V) is applied across the WE and the CE.

For both deposition processes, an Ag/AgCl reference electrode (RE) was used to maintain precise applied voltages. In order to prevent unwanted deposition on the connection pads, a stop-off lacquer was applied over the pads prior to deposition steps (Before/After, FIG. 8E). FIGS. 8F-G show the completed pH and glucose sensors ready to be transferred to the bioreactor.

Figure 9C:
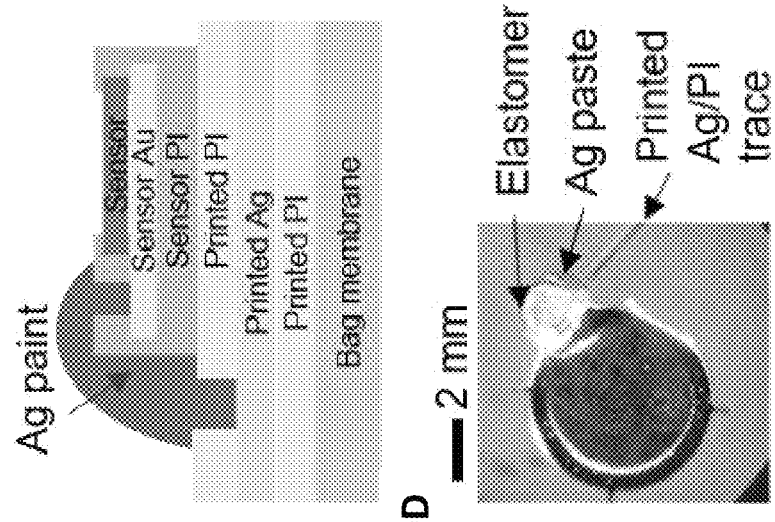
FIGS. 9A-9D illustrate selective and deterministic sensor integration and interconnects in accordance with one or more exemplary embodiments of the present invention.
Figures 9B, 9D:
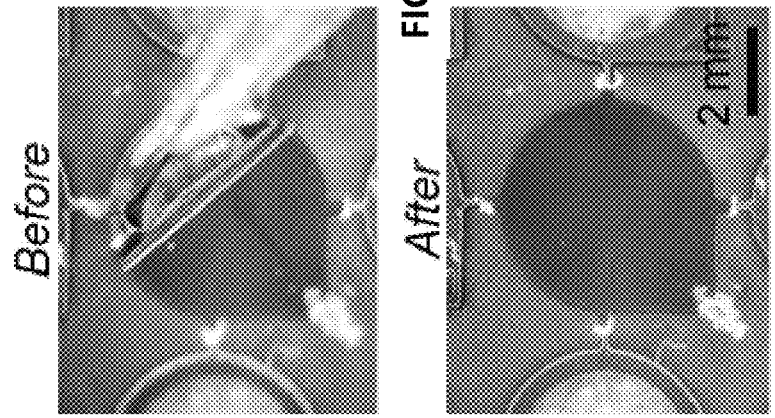
Figure 9A:
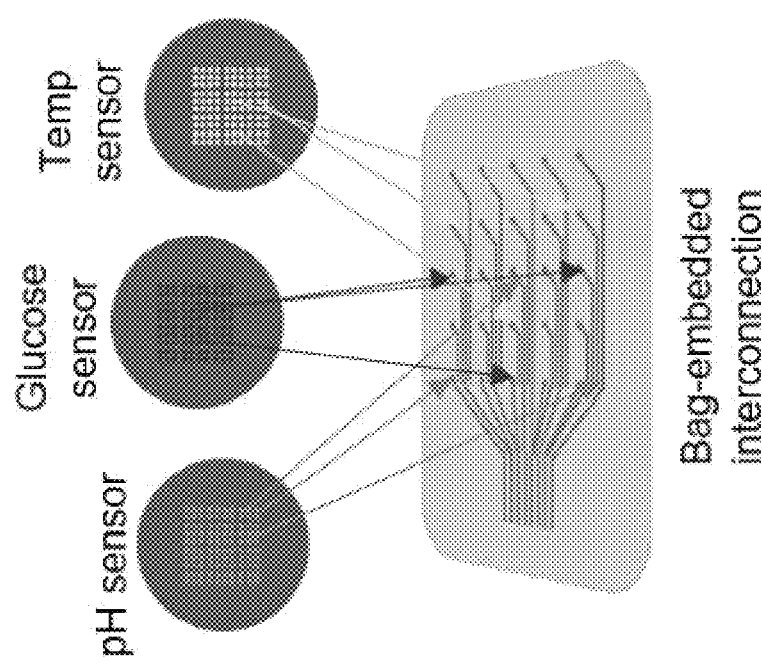

As noted, to facilitate the tear-off of the selected sensor without affecting other sensors, the contour of the conductive bridges exhibits the shallowed PI's width in the middle (FIG. 8C), and the effectiveness of this unique design feature is now described. The 10×10 sensor arrays have been prepared at wafer-scale and the PDMS-coated wafer as well as the tear-off feature allow individual sensors to be removed from the donor wafer and integrated with the bioreactor. This assembly concept is illustrated in FIG. 9A. FIG. 9B captures the moment the completed sensor pixel is peeled from the wafer using pointed tweezers. The weak adhesion between PI and PDMS allows the sensor to be released effortlessly, whereas the tear points guide the controlled fracture of the bridges. FIG. 9C schematically depicts the method with which the transferred sensor is electrically connected to the printed interconnection embedded in the bioreactor. Ag paint is applied over the connection pads on both the sensor and the interconnection (FIG. 9D) and allowed to dry for 30 minutes followed by an elastomer coating to expose only the sensor material to the culture medium.

FIG. 10A shows an exemplary temperature sensor circuitry, which operates via the Wheatstone bridge topology. The fabricated Pt thermistor is connected in the place of Rx in the Wheatstone bridge (Block 2). Block 1 is an input voltage buffer that provides voltage when triggered by a power bus from the microcontroller. Block 2 uses the principles of resistive voltage division and the exponential dependence of temperature on resistance to calculate the temperature. The output voltage is by definition:

$$V_{out} = V_{in}\left(\frac{R2}{R2+R3} + \frac{Rx}{R1+Rx}\right) \quad \text{(Equation 1)}$$

Because Rx is the only unknown, it can be calculated from Equation 1. Once Rx is known, the temperature can be determined by the following relation:

$$\ln\left(\frac{Rx}{R}\right) = \beta\left(\frac{1}{T} - \frac{1}{T_0}\right) \quad \text{(Equation 2)}$$

Block 3 is a differential amplifier that calculates the Wheatstone bridge output voltage.

FIG. 10B describes a simplified version of the pH sensor circuit. The pH sensor includes a working and reference electrode, which are designed to produce a differential voltage proportional to the solution's pH. Because the reference electrode is non-conductive, it is referenced to ground, precluding the implementation of a differential amplifier. Instead, the voltage at the working electrode is measured with respect to the reference electrode by a non-inverting, low pass amplifier, with the gain set as the ratio $$Av = \left(1 + \frac{R1}{R2}\right).$$

The voltage transmitted to the Arduino is thus:

$$V_{out} = (WE - RE)\left(1 + \frac{R1 \parallel (-jwc)}{R2}\right) \quad \text{(Equation 3)}$$

FIG. 10C depicts the amperometric circuit designed for the glucose sensor. The circuit is an improvement upon simple amperometric methods because it allows for real time monitoring of the applied cell potential and uses a load independent voltage buffer to stabilize the input voltage. The overall function of the circuit is to supply a differential voltage between the reference and working electrode in order to facilitate glucose ion transduction on the counter electrode.

Block 1 is a summing amplifier that receives a voltage from a power bus and sets the output line to the inverted sum of the input voltage and the reference electrode voltage. Block 2 inverts this voltage back to positive polarity. Block 3 stabilizes the voltage to be fed into the working electrode. Block 4 stabilizes the reference electrode voltage before being fed into Block 1. Finally, Block 5 transduces the output current between Counter and Ground into a voltage that is provided to the microcontroller. This voltage is calculated from Ohm's Law given the value of the transduction resistor.

The overall structure of the smart bioreactor sensing circuitry is shown in FIG. 10D. Each sensor in the sensor array is interfaced with a unique signal transduction circuit as outlined. Once the signals are converted to raw voltages, the microcontroller in the Bluetooth module will select the signal via multiplexer and sample it with an ADC. After sampling, the digital voltage will be sent to a computer running a C application showing a spatial map of the sensor values in real time.

Figure 11:
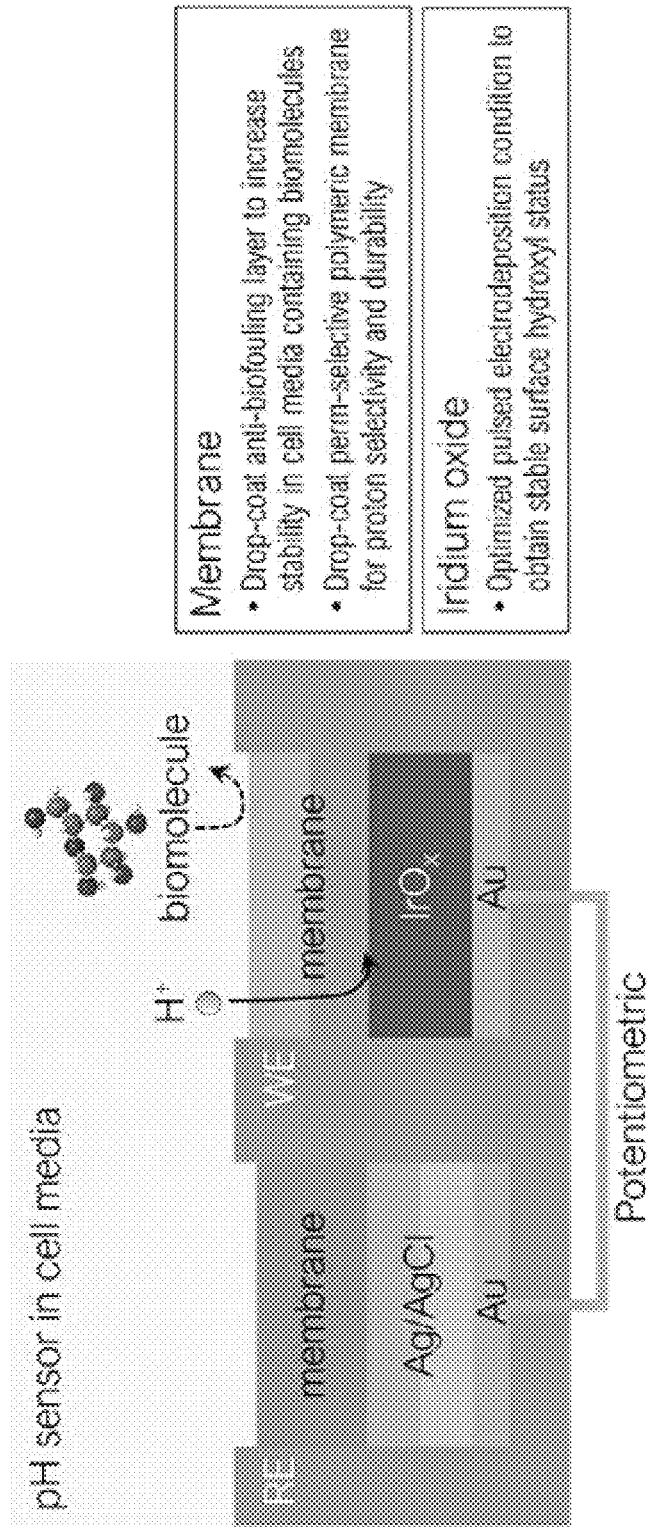
FIG. 11 illustrates the enabling technologies for the iridium oxide ($IrO_x$) sensor material and top membranes in accordance with one or more exemplary embodiments of the present invention.

Overall pH sensing capability in cell culture media was improved. Various strategies lead to the surface stability of the sensor, resulting in monitoring subtle pH for seven days. Overall, FIG. 11 illustrates the enabling technologies for the $IrO_x$ sensor material and top membranes.

In prior embodiments, an $IrO_x$ pH sensor was fabricated via pulsed electrodeposition. Even though the method successfully enhanced surface conformality of the film electrode by minimizing oxygen evolution, it still has a long-term stability issue. This instability is due to the film's surface hydroxyl status that changes over time in the media and even in air, resulting in the change in the voltage signal.

Figure 12D:
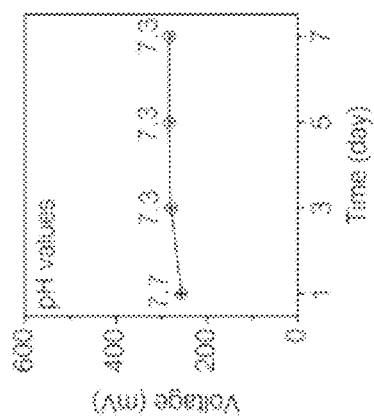
FIGS. 12A-12D show the enhanced stability of $IrO_x$ film electrode.
Figure 12C:
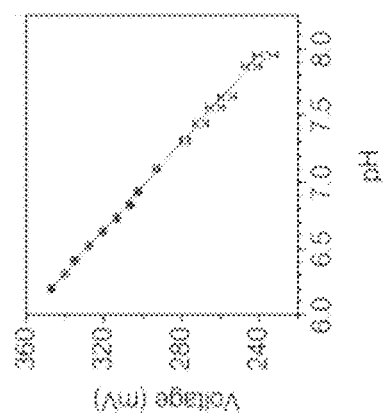
Figure 12B:
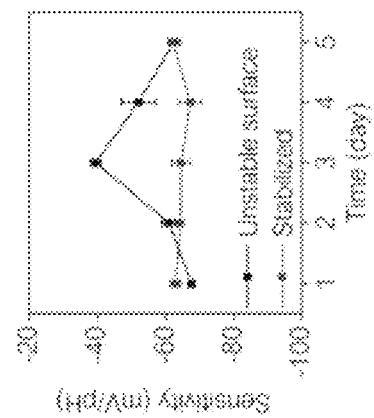
Figure 12A:
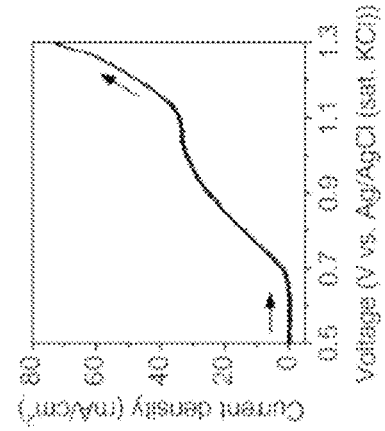

To increase the surface stability, an applying voltage of the pulsed condition was controlled as shown in FIG. 12A. In prior embodiments, it was fixed at a $V_{CN}$=1.1 V. FIG. 12A shows a linear sweep voltammogram of oxidation reactions at the surface of Au in $IrO_x$ deposition solution. The reaction starts from an oxidation voltage of 700 mV and slowly increases up to near 1.1 V where an unwanted oxygen evolution occurs.

The voltage was changed from 0.7 to 1.1 V and presented the result in FIG. 12B. Without voltage optimization, the sensitivity highly fluctuates in a range of −40 to −65 mV/pH. An optimized sensor that used a 900 mV as the $V_{ON}$ showed enhanced stability, while the sensor was stored in air. Considering most commercial glass electrodes and film-type sensors are supposed to be stored in a buffer solution before use, the present sensor can be provided with the circuit in dried status.

The sensor also provides a sensing result measured in a subtle pH range (FIG. 12C). Since the cell productivity is highly affected by any small changes of pH, the voltage was measured with different pH buffer solutions of pH 6 to with a 0.1-0.2 discrepancy. The stabilized film electrode showed a super-Nernstian response (−61 mV/pH) and 0.25 pH accuracy. FIG. 12D presents the voltage change along with its pH value, which changed little for seven days, indicating that the present sensor can work without calibration before use.

In prior embodiments, Nafion was used as a cation-selective membrane. Despite its perm-selectivity, high robustness, and biocompatibility, other cations including $K^+$ can go through the membrane in cell culture media which includes various cations ($Na^+$, $K^+$, $Zn^{2+}$, $Fe^{2+}$, etc.) from inorganic salts added for the osmotic balance. To minimize this disturbance, an ion-selective membrane (ISM) was adopted for improving selectivity and obtaining accurate result.

The $H^+$-selective membrane cocktail was prepared by mixing 10 wt % hydrogen ionophore I, 89.3 wt % 2-nitrophenyl octyl ether (o-NPOE), and 0.7 wt % potassium tetrakis(4-chlorophenyl) borate. The solution was sonicated for ten minutes and homogenized with a vortex mixer, while the optimized $IrO_x$ surface was being hydrated in pH 7 solution. Afterwards, the volume of 2 μm cocktail of each membrane solution was drop-coated on the $IrO_x$ surface and dried overnight. FIGS. 13A-C shows the voltage result of three samples of each membrane-coated sensor in cell media. The pH difference to the glass pH electrode (FIG. 13A) decreased from 0.4 to 0.1 with the ISM (FIG. 13C), indicating the decreased interference with other cations.

The inventive pH sensor works as a potentiometric sensor that reads a voltage difference between working and reference electrodes (WEs, REs). Therefore, a high stability is required for the REs even higher than the working electrode, making sure to reduce any signal errors and sensor failure. However, commercially available REs are fragile, bulky, and thus not seamlessly adaptable for the disposable bioreactor.

FIG. 14A shows a photo of the commercial rod RE, and a thin film RE of the present invention that addresses these problems. The present RE film comprises thin AgCl on Ag layer (FIG. 11), providing a highly small form factor that occupies a smaller area (FIG. 14B). This film configuration comes with a critical issue on its voltage stability due to the unused of a filling solution. Annealing of the Ag film and chemical stabilizing steps of the film structure were adopted, resulting in resolving detachment of the films from the substrate and stable voltage for one week in phosphate-buffered saline (PBS) solution (FIG. 14C). In this way, the present film RE film has a very small voltage deviation less than 0.5 mV for 18 days (FIG. 14D). To use the present RE for the potentiometric sensor, polyvinyl butyral (PVB) was applied to provide insensitivity to pH change and used in muscle cell media.

Figures 15A, 15B, 15C:
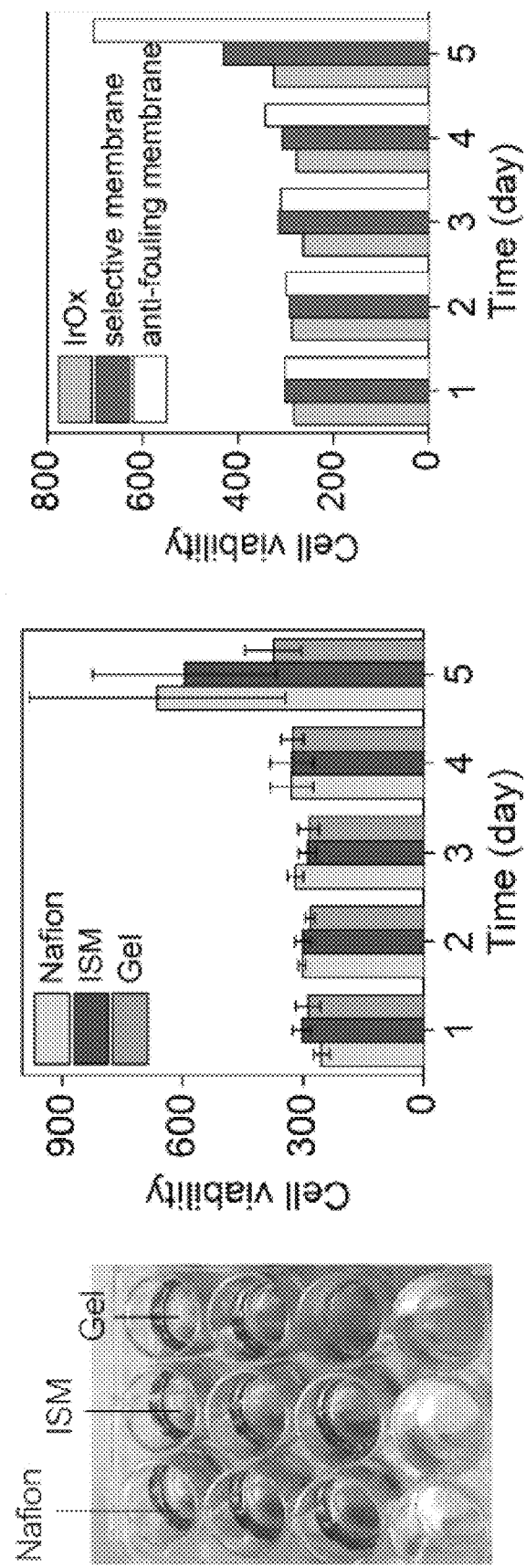
FIGS. 15A-15C show the effect of different membranes on C2C12 cell viability.

The functionality of an anti-biofouling membrane pH sensor in cell media was tested. All the membranes, including Nafion, ISM, and gel, are highly acceptable and biocompatible for the use in cell culture media. pHEMA (poly(2-hydroxyethyl methacrylate) was used for the anti-biofouling effect. FIG. 15A is a photo partially showing a 24-well plate coated with the different membranes coated on the bottom. A 20-µL solution of 0.5 vol % Nafion was drop-coated for 30 minutes and dried in air for one hour after removing residual.

The same coating protocol was followed for the $H^+$-ISM and pHEMA membranes, but they were dried at 80° C. Afterwards, 1 mL C2C12 growth media was dropped with a same number of the cells. Cell viability was measured in a daily basis by dying the cells with a 1:9 vol % PrestoBlue:growth media solution.

Before measurement, the plate solutions were incubated for more than ten minutes at 37° C. The viability results measured at a recommended condition (Fluorescence; excitation 560 nm, emission 590 nm) presented in FIG. 15B shows that all the membranes are compatible with cell culture media.

Even though the Nafion and ISM showed better viability, its deviation is a lot higher than that of the gel-coated surfaces. This could be due to a degradable effect of the cell culture to the selective membranes. Therefore, the present pH electrode coated with the anti-biofouling membrane of a top of the selective layer showed a higher productivity than the $IrO_x$ electrode or the film with one selective membrane (FIG. 15C).

Long-term sensing capability has been achieved, as the present invention improves upon the stability, selectivity, and biocompatibility of the pH sensing electrode and RE. FIG. 16A shows the improved stability in voltage signal measured in cell media for seven days. Conventional sensors lose sensing capability in a short period of time due to the unstable surface, but the present sensor showed seven-day stable reading of the voltage. As a result, the sensor was able to read the pH of C2C12 cell media for seven days as shown in FIG. 16B.

The results (day 1: pH=8.00, day 7: 7.95) were compared to a bulky glass electrode (day 1: 8.25, day 7: 8.14), indicating that the pH difference was only 0.2 pH. FIG. 16C shows that the present sensor provides a small and thin form factor, which was adopted in cell culture dishes, while the commercial sensor is bulky and used with a filling solution (left side of the sensor). Collectively, the present pH electrode has stable and cell-compatible surfaces to ensure a long-term measurement of pH in cell media.

Figure 17C:
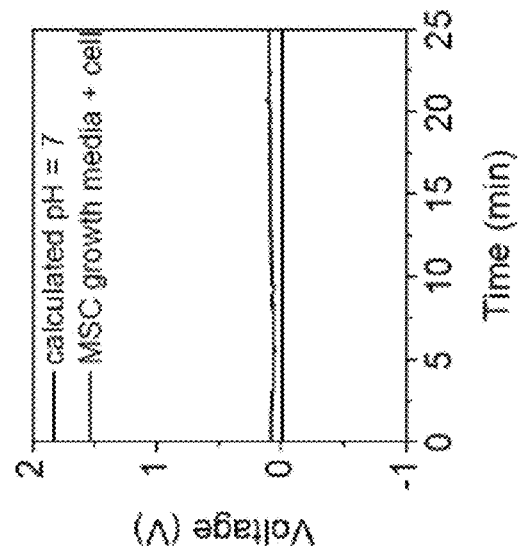
FIGS. 17A-17C show the adaptability of the present sensor to a muscle stem cell (MuSC) environment.
Figure 17B:
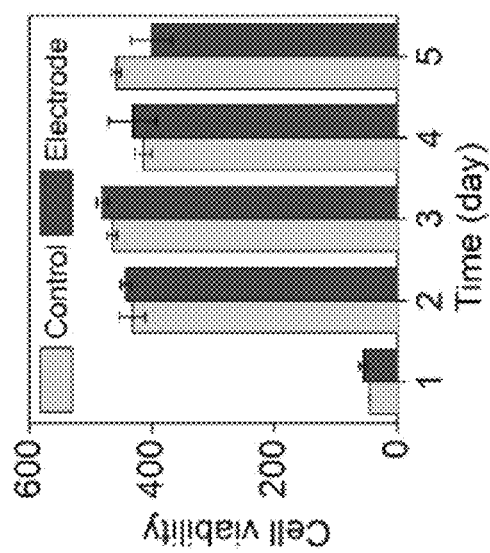
Figure 17A:
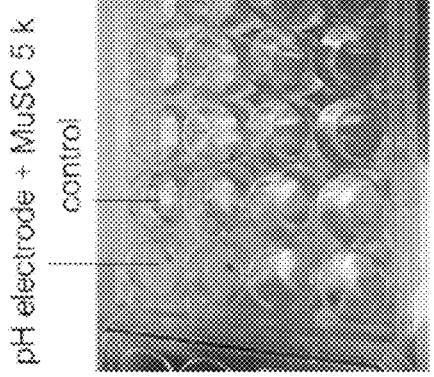

The present optimized sensor was used with muscle stem cells (MuSC) to perform cell viability measurements. For the experiment, mice cells were seeded in 1 mL growth media using a multi-well cell culture plates with 24 covered wells. FIG. 17A shows the cell plate used for the viability test. First, the plate was prepared by fixing the present $IrO_x$ pH electrodes on the bottom of the plate with Ecoflex. The two different membranes were coated on the top of the sensor. The surfaces of the sensor and control plates were coated with laminin mouse protein and collagen I (rat tail) with 0.3:8.3 µl/ml volume ratio in PBS solution. After a 30-minute immersion, the plates were cleaned with PBS and dried in air for 30 minutes. The same number of cells (5 k) were seeded into the wells with 1 mL cell culture media. The growth media is composed of F10 medium containing 20% horse serum, and 1% penicillin/streptomycin. Lastly, a small amount of basic fibroblast growth factor (bFGF; 1 µl/ml) was added in a daily basis. FIG. 17B shows the viability of the MuSC grown for five days in an incubator (temperature: 37° C., oxygen concentration: 20%).

The results showed that the present electrodes rarely affect the cell proliferation at least for three days compared to the control data. Also, the voltage signal of the present sensor in the MuSC media showed a stable reading, which was calculated as near pH=7 (FIG. 17C). The pH measured with present sensor was slightly lower than commercial sensor (pH=7.7), which may be due to the coating layer on the top of the sensor before loading the MuSC.

The present invention further comprises improved functionality of an inorganic glucose sensor. A controlled voltage of the sensing voltage of a PdFe glucose sensor was examined.

In prior embodiments, palladium iron (PdFe) inorganic film was used a glucose sensor. The film electrode deposited by using cyclic voltammetry showed a high sensitivity to glucose in a concentration range of 1-55 mM that covers a normal low and high glucose levels used for culturing cells. However, since the film monitored glucose levels based on an amperometric sensing mechanism, the signal appears as a current differential while the circuit applies a certain voltage for detecting glucose levels. Unlike the potentiometric sensors, the voltage should be as low as possible not to interfere with other bio-chemicals in the cell culture solution. In the present invention, focus was on lowering the applying voltage that was optimized before to 0.26 V by characterizing the film as well as by investigating different linearity dependent on the voltage level.

Figure 18C:
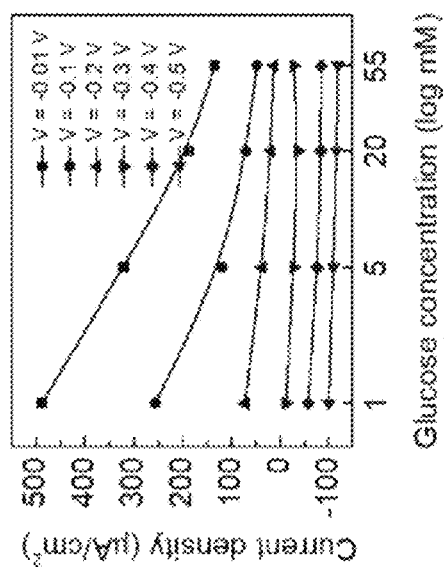
FIGS. 18A-18C illustrate inventive glucose sensor characterizations.
Figure 18B:
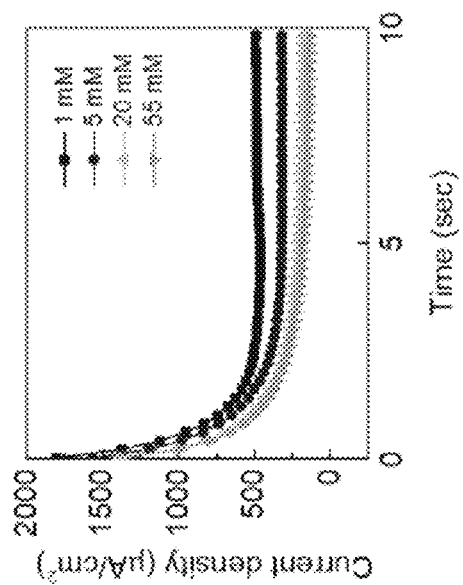
Figure 18A:
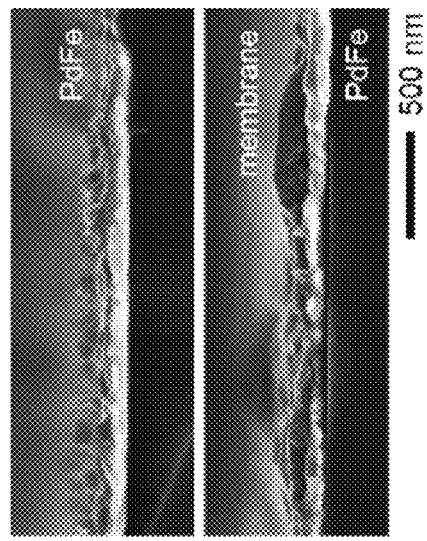

FIG. 18A shows SEM images of the electro-deposited PdFe films with and without coating a membrane on the top. 5 wt % Nafion was used for selectivity and durability of the thin film sensor. As can be seen, the film was covered by the thick membrane, which compensates any surface roughness and may reduce an unwanted oxidation of Fe in the film. Sensing capability of the resulting electrode was investigated with chronoamperometry that applies a fixed voltage for a short period of time (FIG. 18B). At −0.01 V, which is a lot lower than the previous condition, the voltages appear different clearly according to the glucose levels, while their response was stabilized in several seconds. Such improved sensing capability was optimized by controlling the voltage levels from −0.01 to 0.5 V as can be seen in FIG. 18C.

Collectively, the present sensor showed a linear response at −0.01, −0.1, and −0.2 V with sensitivity from −34 through −119 to −208 µA/log(mM)·cm². The sensitivity was comparable with the previous result with a lower voltage condition. At the more negative voltage, none of linear response was monitored, indicating there were no oxidation reactions.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

We claim:

1. A smart bioreactor system comprising:
   a flexible bioreactor comprising a flexible bioreactor membrane, the flexible bioreactor having a pre-containment configuration and a containment configuration;
   a sensing system integrated onto a sensing portion of an inner surface of the flexible bioreactor membrane of the flexible bioreactor and comprising:
      a membrane-embedded flexible electronic telemetry unit; and
      a flexible, nanomembrane, multimodal sensing platform comprising an array of flexible nanomembrane sensors; and
   a rocking unit;
   wherein at least a portion of the flexible nanomembrane sensors of the array each comprise:
      a sensor area;
      a tab for electrical connection with the membrane-embedded flexible electronic telemetry unit; and
      one or more bridges for electrical connection with a respective one or more adjacent flexible nanomembrane sensors of the array;
      wherein at least a portion of the bridges of the array have a tear point formation wherein a thickness of a respective bridge at the tear point formation is designed to facilitate tear-off between two adjacent sensors;
   wherein, in the pre-containment configuration, the sensing portion of the flexible bioreactor membrane is planar, so the multimodal sensing platform of the sensing system is also planar;
   wherein, in the containment configuration, the bioreactor is configured to contain a biologically active environment, and as such, the sensing portion of the flexible bioreactor membrane is non-planar, conforming to the contained biologically active environment, so the multimodal sensing platform of the sensing system is also non-planar; and
   wherein, in the containment configuration, the non-planar multimodal sensing platform of the sensing system is configured to:
      provide spatial data of wireless real-time data representative of modalities of the biologically active environment moving within the flexible bioreactor resultant from rocking of the bioreactor via the rocking unit; and
      be in direct contact with the moving biologically active environment contained within the flexible bioreactor.

2. The smart bioreactor system of claim 1, wherein the flexible bioreactor membrane comprises a flexible layer configured to cooperatively flex to the movement of the biologically active environment contained therein when the flexible bioreactor is in the containment configuration; and
   wherein the modalities of the biologically active environment are selected from the group consisting of pH, glucose level, and temperature of the biologically active environment.

3. The smart bioreactor system of claim 1, wherein the membrane-embedded flexible electronic telemetry unit is encapsulated within a silicon-based elastomer;
   wherein the flexible, nanomembrane, multimodal sensing platform is encapsulated within a biocompatible polymer; and
   wherein the sensing system is further configured to provide a means to monitor large area culture qualities through the spatial sensing capabilities, culture compatibility, and scalability.

4. The smart bioreactor system of claim 3, wherein the flexible, nanomembrane, multimodal sensing platform comprises an open-mesh serpentine network.

5. The smart bioreactor system of claim 4, wherein the array of flexible nanomembrane sensors include super-Nernstian pH sensors, each pH sensor comprising an iridium oxide ($IrO_x$) film deposited on a platinum electrode.

6. The smart bioreactor system of claim 4, wherein the array of flexible nanomembrane sensors include glucose sensors, each glucose sensor comprising glucose oxidase enzyme (GOD) and a platinum electrode.

7. The smart bioreactor system of claim 4, wherein the array of flexible nanomembrane sensors include temperature sensors, each temperature sensor comprising a thin-film platinum electrode.

8. The smart bioreactor system of claim 4, wherein the array of flexible nanomembrane sensors include:
   pH sensors, each pH sensor comprising an iridium oxide ($IrO_x$) film deposited on a platinum electrode;
   glucose sensors, each glucose sensor comprising glucose oxidase enzyme (GOD) and a platinum electrode; and
   temperature sensors, each temperature sensor comprising a thin-film platinum electrode.

9. A smart bioreactor system comprising:
   a sensing system comprising:
      a flexible electronic telemetry unit; and
      a flexible, nanomembrane, multimodal sensing platform comprising an array of a platform number of flexible nanomembrane sensors, the array formed from a wafer of a wafer number of flexible nanomembrane sensors, the wafer number larger than the platform number; and
   a rocking unit;
   wherein the flexible nanomembrane sensors of the array each comprise:
      a sensor area;
      an exposed metal tab for electrical connection with the flexible electronic telemetry unit; and
      bridges, one each for electrical connection with a respective adjacent flexible nanomembrane sensor of the array;
      wherein each bridge has a tear point formation wherein a thickness of the bridge at the tear point formation is narrowed so as to facilitate tear-off between two previously adjacent sensors, one of the previously adjacent sensors being a part of the array and the other of the previously adjacent sensors being a part of the wafer but not of the array;
   wherein the sensing system is configured to:
      provide spatial data of wireless real-time data representative of modalities of a biologically active environment moving within a flexible bioreactor resultant from rocking of the bioreactor via the rocking unit;

be embedded on an inner surface of the flexible bioreactor and in direct contact with the biologically active environment within the rocking flexible bioreactor; and monitor the quality of biological products in the biologically active environment by a mapping of conditions using the array of flexible nanomembrane sensors.

10. The smart bioreactor system of claim 9, wherein the array of flexible nanomembrane sensors include at least one pH sensing mechanism including a reference electrode (RE), a working electrode (WE) and an amplifier;

wherein the pH sensing mechanism is designed to produce a differential voltage proportional to the pH of the biologically active environment.

11. The smart bioreactor system of claim 9, wherein the array of flexible nanomembrane sensors include at least one amperometric glucose sensing mechanism including a reference electrode (RE), a working electrode (WE) and a counter electrode (CE);

wherein the amperometric glucose sensing mechanism is designed to supply a differential voltage between the RE and the WE in order to facilitate glucose ion transduction on the CE.

12. A bioreactor system comprising:

a flexible bioreactor configured to contain a biologically active environment; and the smart bioreactor system of claim 9;

wherein the sensing system:

provides the spatial data of wireless real-time data representative of modalities of the biologically active environment moving within the flexible bioreactor resultant from rocking of the flexible bioreactor via the rocking unit;

is embedded on the inner surface of the flexible bioreactor and is in direct contact with the biologically active environment within the rocking flexible bioreactor; and monitors the quality of the biological products in the biologically active environment by the mapping of conditions using the array of flexible nanomembrane sensors.

13. A bioreactor system for the cultivation of stem cells comprising:

a flexible bioreactor configured for the cultivation of stem cells; and the smart bioreactor of claim 9;

wherein the biologically active environment is configured for the cultivation of stem cells.

* * * * *